US010051357B2

(12) United States Patent
Silvestri et al.

(10) Patent No.: US 10,051,357 B2
(45) Date of Patent: Aug. 14, 2018

(54) PRESSURE EQUALIZATION IN EARPHONES

(71) Applicant: BOSE CORPORATION, Framingham, MA (US)

(72) Inventors: Ryan C. Silvestri, Franklin, MA (US); Joseph H. Cattell, Somerville, MA (US)

(73) Assignee: BOSE CORPORATION, Framingham, MA (US)

(*) Notice: Subject to any disclaimer, the term of this patent is extended or adjusted under 35 U.S.C. 154(b) by 0 days.

(21) Appl. No.: 15/008,803

(22) Filed: Jan. 28, 2016

(65) Prior Publication Data

US 2017/0223443 A1 Aug. 3, 2017

(51) Int. Cl.

| | |
|---|---|
| ***A61F 11/06*** | (2006.01) |
| ***H04R 1/10*** | (2006.01) |
| ***H04R 1/28*** | (2006.01) |

(52) U.S. Cl.

CPC ......... *H04R 1/1016* (2013.01); *H04R 1/1091* (2013.01); *H04R 1/2823* (2013.01); *H04R 1/2826* (2013.01); *H04R 1/2849* (2013.01); *H04R 1/1083* (2013.01); *H04R 2460/01* (2013.01); *H04R 2460/11* (2013.01)

(58) Field of Classification Search

CPC H04R 1/1016; H04R 1/2823; H04R 2460/01; H04R 2460/11

See application file for complete search history.

(56) References Cited

U.S. PATENT DOCUMENTS

| | | | | |
|---|---|---|---|---|
| 4,403,120 | A * | 9/1983 | Yoshimi | H04R 1/225 181/129 |
| 5,208,868 | A | 5/1993 | Sapiejewski | |
| 8,594,351 | B2 | 11/2013 | Harlow et al. | |
| 8,989,427 | B2 | 3/2015 | Silvestri et al. | |
| 2002/0080990 | A1* | 6/2002 | Lin | H04R 1/1016 381/380 |
| 2012/0314882 | A1* | 12/2012 | Sibbald | H04R 1/1016 381/71.6 |
| 2013/0315411 | A1 | 11/2013 | Annunziato et al. | |
| 2016/0206477 | A1* | 7/2016 | Davidson | A61F 11/08 |

FOREIGN PATENT DOCUMENTS

| | | | |
|---|---|---|---|
| EP | 3035700 | A1 | 6/2016 |
| WO | 03010993 | A2 | 2/2003 |
| WO | 2014197294 | A1 | 12/2014 |
| WO | 2015022817 | A1 | 2/2015 |
| WO | 2015138829 | A1 | 9/2015 |

OTHER PUBLICATIONS

International Search Report dated Apr. 24, 2017 for International Application No. PCT/US2017/015255.

* cited by examiner

*Primary Examiner* — Andrew L Sniezek

(74) *Attorney, Agent, or Firm* — Patterson + Sheridan, LLP

(57) ABSTRACT

An earphone includes an acoustic transducer and a housing that includes a first acoustic chamber acoustically coupled to a first side of the acoustic transducer and a second acoustical chamber acoustically coupled to a second side of the acoustic transducer. The housing further includes a port acoustically coupling the first acoustic chamber and the second acoustic chamber. Acoustic resistive material is positioned proximate the port.

23 Claims, 8 Drawing Sheets

PRIOR ART

PRESSURE EQUALIZATION IN EARPHONES

I. FIELD OF THE DISCLOSURE

This description relates generally to earphones, and more specifically, to earphones that include port structures to equalize a frequency response.

II. BACKGROUND

As shown in FIG. 1, a human ear 10 includes an ear canal 12 which leads to the sensory organs (not shown). The pinna 11, the part of the ear outside the head, includes the concha 14, the hollow next to the ear canal 12, defined in part by the tragus 16 and anti-tragus 18. An earphone is generally designed to be worn over the pinna, in the concha, or in the ear canal.

During high pressure and high volume displacement events, air pressure can build up in the earphone and degrade sound quality. For example, certain high pressure and high volume displacement events (e.g., when an earphone is inserted or removed or repositioned in a user's ear) can cause a perceptible squeal or other sound distortion. The distortion may vary from person to person, as differences in head sizes, ear shapes and ear sizes result in variation in the response and output of the earphones across users. One approach to mitigate these issues is to include a pressure equalization port that serves to relieve air pressure that could build up within the earphone.

III. SUMMARY

All examples and features mentioned below can be combined in any technically possible way.

In one aspect, an earphone includes an acoustic transducer and a housing comprising a first acoustic chamber acoustically coupled to a first side of the acoustic transducer and a second acoustic chamber acoustically coupled to a second side of the acoustic transducer. A port acoustically couples the first acoustic chamber and the second acoustic chamber. Acoustic resistive material is positioned proximate the port.

Embodiments may include one of the following features, or any combination thereof. In an example, an area of the port ranges from about 0.4×10−6 m2 to about 40×10−6 m2. A length of the port may range from about 0.1 millimeters to about 10 millimeters. The acoustic resistive material may have an impedance that ranges from about 10 MKS Rayls to about 20,000 MKS Rayls. The acoustic resistive material comprises at least one of: a plastic, a textile, a metal, a permeable material, a woven material, a screen material, and a mesh material. The port may have a resistive component of acoustic impedance of between about $2\times10^6$ acoustic ohms and about $8\times10^7$ acoustic ohms at low frequencies.

Embodiments may include one of the following features, or any combination thereof. According to an example, the earphone includes active noise cancellation circuitry. The first acoustic chamber may be separated from the second acoustic chamber by the acoustic transducer. A frequency response of the earphone may be substantially linear at low frequencies. A frequency response of the earphone may be approximately the same at high and low signal values at frequencies below 100 Hz. A difference in a frequency response of the earphone at low signal values and a frequency response of the earphone at high signal values may be less than 3 dB at frequencies between 10 and 100 Hz. The port may provide damping in a frequency response of the acoustic transducer at high frequencies.

In another aspect, an acoustic transducer and active noise cancellation circuitry. A housing comprises a first acoustic chamber that at least partially encloses the acoustic transducer. A port is proximate the first acoustic chamber. The port has an area ranging from about $0.4\times10^{-6}$ m$^2$ to about $40\times10^{-6}$ m$^2$. An acoustic resistive material is positioned proximate the port. Embodiments may include one of the following features, or any combination thereof. In an example, the port acoustically couples the first acoustic chamber to an environment external to the earphone. The port of an example acoustically couples the first acoustic chamber to a second acoustic chamber. A length of the port ranges from about 0.1 millimeters to about 10 millimeters. The acoustic resistive material has an impedance that ranges from about 10 MKS Rayls to about 20,000 MKS Rayls. The acoustic resistive material comprises at least one of: a plastic, a textile, a metal, a permeable material, a woven material, a screen material, and a mesh material. The port has a resistive component of acoustic impedance of between about $2\times10^6$ acoustic ohms and about $8\times10^7$ acoustic ohms at low frequencies. A frequency response of the earphone may be substantially linear at low frequencies. A frequency response of the earphone may be approximately the same at high and low signal values at frequencies below 100 Hz. A difference in a frequency response of the earphone at low signal values and a frequency response of the earphone at high signal values may be less than 3 dB at frequencies between 10 and 100 Hz. The port may provide damping in a frequency response of the acoustic transducer at high frequencies.

Other features, objects, and advantages will become apparent from the following detailed description and drawings.

IV. BRIEF DESCRIPTION OF THE DRAWINGS

V. DETAILED DESCRIPTION

Figure 1:
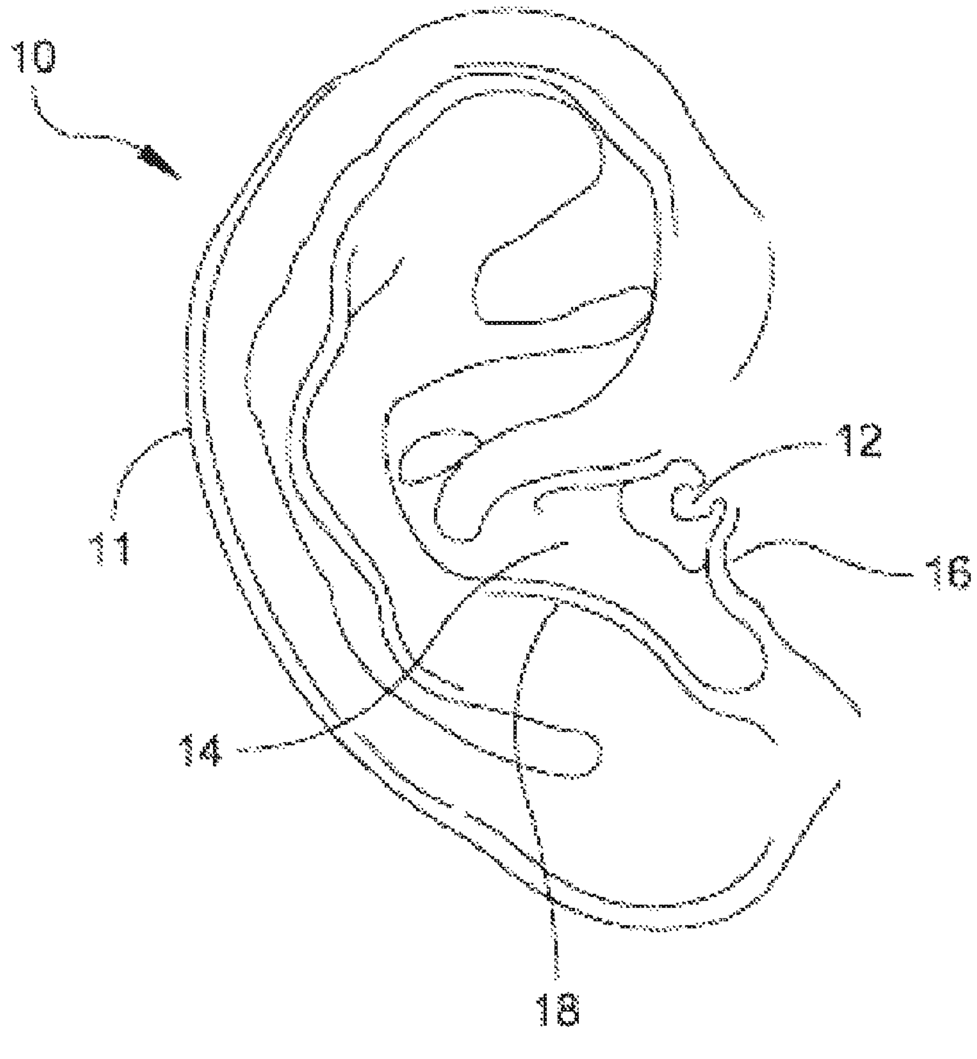
FIG. 1 shows a human ear.

An earphone refers to a device that fits around, on, or in an ear and that radiates acoustic energy into the ear canal. Earphones are sometimes referred to as headphones, earpieces, headsets, earbuds or sport headphones, and can be wired or wireless. An earphone includes an acoustic driver to transduce audio signals to acoustic energy. An around or on the ear earphone uses an acoustic driver that is typically larger than a driver used in an in-ear earphone (e.g., an earphone that seats within the pinna). While the figures and descriptions following show a single earphone, an earphone may be a single stand-alone unit or one of a pair of earphones, one for each ear. An earphone may be connected mechanically to another earphone, for example by a headband or by leads that conduct audio signals to an acoustic driver in the earphone. An earphone may include components for wirelessly receiving audio signals. An earphone may include components of an active noise reduction (ANR) system.

Low frequency, high pressure and high volume displacement events in an earphone can sometimes result in an audible artifact, such as a squeal or other distortion. These events occur, for example, when the earphone is inserted into (or onto) or removed from a user's ear, when the user experiences shock or vibration, and/or when the earphone is struck or repositioned while being worn. The distortion may vary from person to person, as differences in head sizes, ear shapes and ear sizes result in variation in the response and output of the earphones across users. In addition, these high volume displacement events are further compounded in an earphone having an ANR system, as the ANR system likewise generates high volume displacements in response.

Several configurations can be used to vent pressures generated in an earphone and reduce fit-to-fit variation of the earphone. For example, around the ear earphones may use a small tube to vent and equalize pressure generated in an ear cup. Similarly, in-ear earphones may use a small hole to vent and equalize pressure. These tubes, openings, vents or holes may be referred to as ports. As discussed in more detail herein, these ports have a complex impedance that includes a resistive and a reactive component (also referred to as a mass or frequency dependent component).

Due to sizing constraints, particularly in in-ear earphones, these ports are typically small in size (in some examples having a diameter of ½ mm or less). Consequently, the port impedance at low frequencies (e.g., below 100 Hz) is dominated by the resistive component and the driver behavior at low frequencies (as characterized, for example, by the frequency response of the driver at low and high signal levels), which in turn may cause the frequency response of the earphones (measured, e.g., at the ear) to become non-linear. The non-linearity may be caused by high particle velocity and displacement through the port, which typically occurs during low frequency, high pressure and high volume displacement events (e.g., donning or doffing the earphones, and/or when sending large voltage signals to the earphone driver). These events can cause changes in the port impedance as well as changes in the driver response, either or both of which may cause the response of the earphones to become non-linear. The non-linear behavior is predominantly seen at low frequencies, but secondary effects may also be seen at high frequencies.

In one example, a port is constructed with a relatively larger diameter hole (compared to traditional earphone ports) and is covered with a resistive mesh to relieve air pressure that could build up in the earphone during the low frequency, high pressure and high volume displacement events described herein. The resistive mesh may include porous material constructed from plastic, textile, and metal, among other woven or permeable materials. In such a port configuration, the resistive component of impedance (and the effective impedance) is higher at lower frequencies than traditional ports. As a result, such a port may reduce particle velocity and displacement through the port (and thus reduce non-linearities in a frequency response of the earphones, particularly at low frequencies where behavior is dominated by the earphone's ports), while maintaining or increasing low frequency output. In some examples (e.g., in applications involving in-ear earphones), the reactive component of impedance is lower at higher frequencies than traditional ports, which aids in providing a port size suitable for an in-ear earphone application. In other applications where space constraints are less of a concern, the reactive component of impedance at higher frequencies may the same as, or higher than, that of traditional ports. At high frequencies (e.g., between 3 kHz and 8 kHz), the port adds damping to the system and helps control resonance. In addition, as described herein, buffet (i.e. physical events such as movement or shaking of the earphone that cause high pressures and can lead to microphone clipping) and other performance characteristics of the earphone are not negatively affected. In some examples, the size of the port as well as the resistivity of the mesh can be adjusted to achieve a desired sound quality and characteristic. One implementation uses a front-to-back port architecture, where the port is positioned between the front and back cavities (also referred to as chambers) of the driver. However other implementations may include a front-to-outside ported design, where the port is positioned between the front cavity and an environment external to the earphone.

Figure 2A:
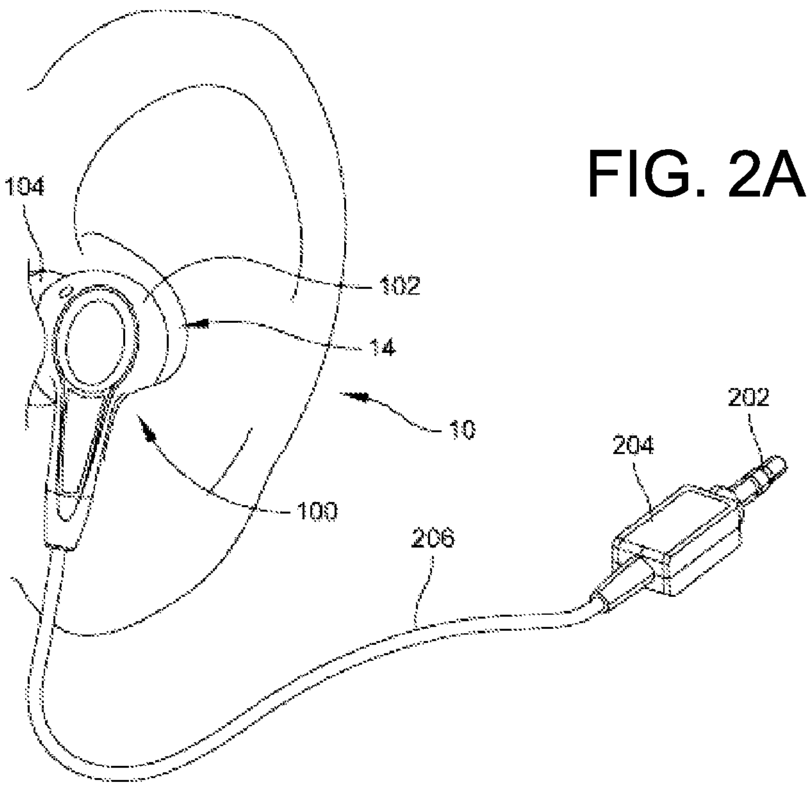
FIG. 2A is a perspective view of an earphone located in the ear.
Figure 2B:
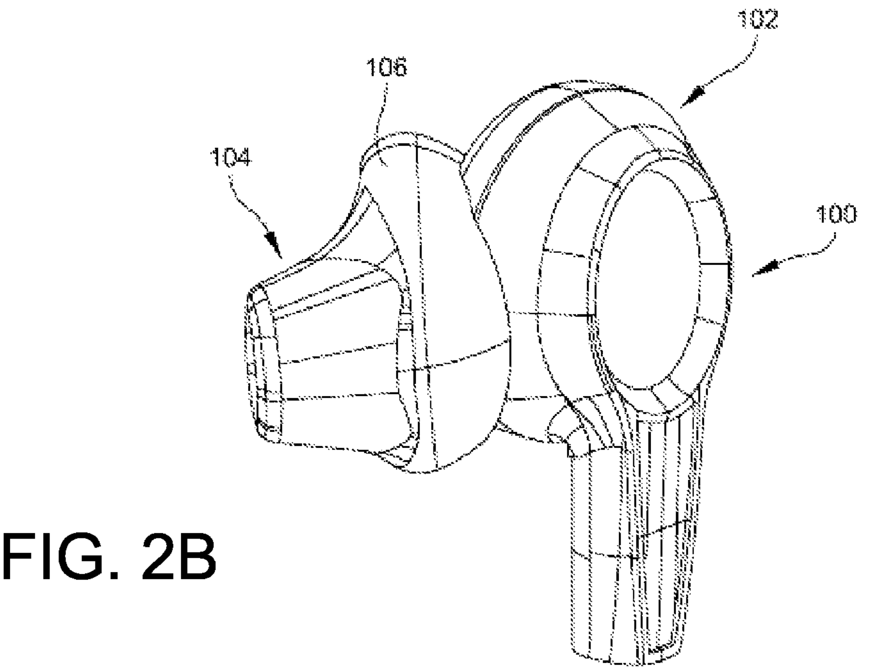
FIG. 2B is an isometric view of an earphone.

As shown in FIGS. 2A and 2B, an earphone 100 may have a housing 102 and a cushion (i.e., ear tip) having a body region 106 designed to fit within the concha 14 of the wearer's ear 10, and an outlet region 104 to be located at the entrance to, or in, the ear canal 12. The ear tip couples the acoustic components of the earphone to the physical structure of a wearer's ear. While the ear tip shown includes a body region 106 and outlet region 104, other ear tip configurations may be used that include these and/or additional regions, or omit these regions. In the case of wired earphones, a plug 202 may connect the earphone to a source of audio signals, such as a CD player, cell phone, tablet, computer, MP3 player, or PDA (not shown), or may have multiple plugs (not shown) allowing connection to more than one type of device at a time. In the case of wireless-enabled earphones, plug 202 may be omitted. An electronics module 204 may include circuitry for modifying the audio signal, for example, by controlling its volume or providing equalization. The circuitry may also provide noise cancellation signals to the earphones. The electronics module 204 may also include switching circuitry, either manual or automatic, for connecting the signals output by one or another of the above mentioned sources to the earphone. In the case of wired earphones, a cord 206 may convey audio signals from the source to the earphones. In some examples, the signals may be communicated wirelessly using Bluetooth® or other wireless communication methods (e.g., Bluetooth® Low Energy (BLE), Near Field Communications (NFC), IEEE 802.1, other local area network (LAN) or personal area network (PAN) protocols, magnetic induction, etc.), and the cord 206 would not be included. Alternatively or additionally, a wireless link may connect the circuitry with one or more of the sources.

Figure 3:
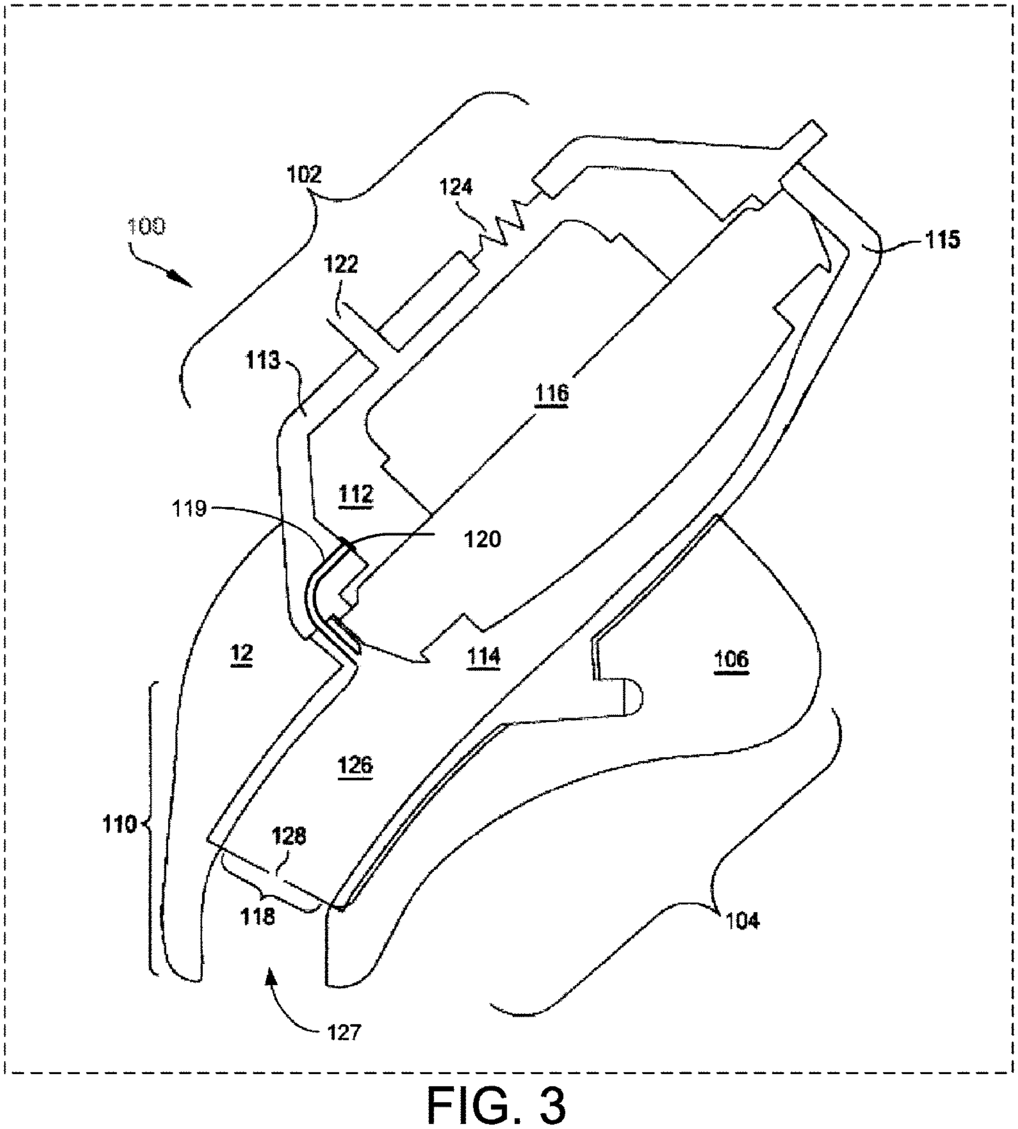
FIG. 3 is a schematic cross section of a first example of an earphone.

As shown in FIG. 3, the housing 102 of the earphone 100 includes a rear acoustic chamber 112 and a front acoustic chamber 114 defined by shells 113 and 115 of the housing, respectively, on either side of a driver (i.e., acoustic transducer) 116. In some examples, a 14.8 mm diameter driver is used. Other sizes and types of acoustic transducers could be used depending, for example, on the desired frequency response of the earphone 100. The driver 116 separates the front and back acoustic chambers 114 and 112. The shell 115 of the housing may extend the front chamber 114 via nozzle 126 to at least the entrance to the ear canal 12, and in some embodiments into the ear canal 12, through the cushion 106. The nozzle may and end at an opening 127 that may include an acoustic resistance element 118. In some examples, the resistance element 118 is located within the nozzle 126 rather than at the end, as illustrated. In other examples, nozzle 126 is omitted.

A pressure equalization (PEQ) port 119 acoustically couples the front acoustic chamber 114 and the rear acoustic chamber 112. The PEQ port 119 serves to relieve air pressure that could be built up within the ear canal 12 and front chamber 114 when (a) the earphone 100 is inserted into (or onto) or removed from the ear 10, (b) a person wearing the earphone 100 experiences shock or vibration, or (c) the earphone 100 is struck or repositioned while being worn. While the PEQ port 119 is shown as having a curved configuration, in other examples, it could be straight (as shown, for example, in FIGS. 5 and 6). The PEQ port 119 has a relatively larger area when compared to previous PEQ port designs, preferably having an area of between about $0.4\times10^{-6}$ $m^2$ to about $40\times10^{-6}$ $m^2$. The area should be large enough to mitigate non-linear behavior of the earphone while fitting within the size constraints of an earphone. The PEQ port 119 preferably has a length of between about 0.1 mm to about 10 mm. Resistive mesh 120 is positioned at or proximate (in another implementation, inside of) the PEQ port 119. As described herein, the resistive mesh 120 may comprise most any porous material and may have an acoustic impedance that ranges from about 10 MKS Rayls to about 20,000 MKS Rayls. While PEQ port 119 is shown in FIG. 3 as venting between the front and back cavities of the driver, in other examples the PEQ port 119 could vent from the front cavity to an environment external to the earphone.

The amount of passive attenuation that can be provided by a ported earphone is often limited by the acoustic impedance through the ports. Generally, more impedance is preferable. However, certain port geometry is often needed to have proper system performance. Ports are used to improve acoustic output, equalize audio response and provide a venting path during overpressure events. Impedance may be changed in a number of ways, some of which are related. Impedance is frequency dependent, and it may be preferable to increase impedance over a range of frequencies and/or reduce the impedance at another range of frequencies. The impedance has two components: a resistive component (DC flow resistance R) and a reactive or mass component $j\omega M$, where $\omega$ is the frequency, and $M=\rho l/A$. M is the acoustic mass; l is the length of the port; A is the cross-sectional area of the port, and $\rho$ is the density of air. The total impedance can be calculated at a specific frequency of interest by determining the magnitude or absolute value of the acoustic impedance $|z|$. The PEQ port 119 preferably has a resistive component of acoustic impedance of between about $2\times10^{6}$ acoustic ohms and about $8\times10^{-7}$ acoustic ohms at low frequencies (e.g., frequencies less than 100 Hz).

Figure 4:
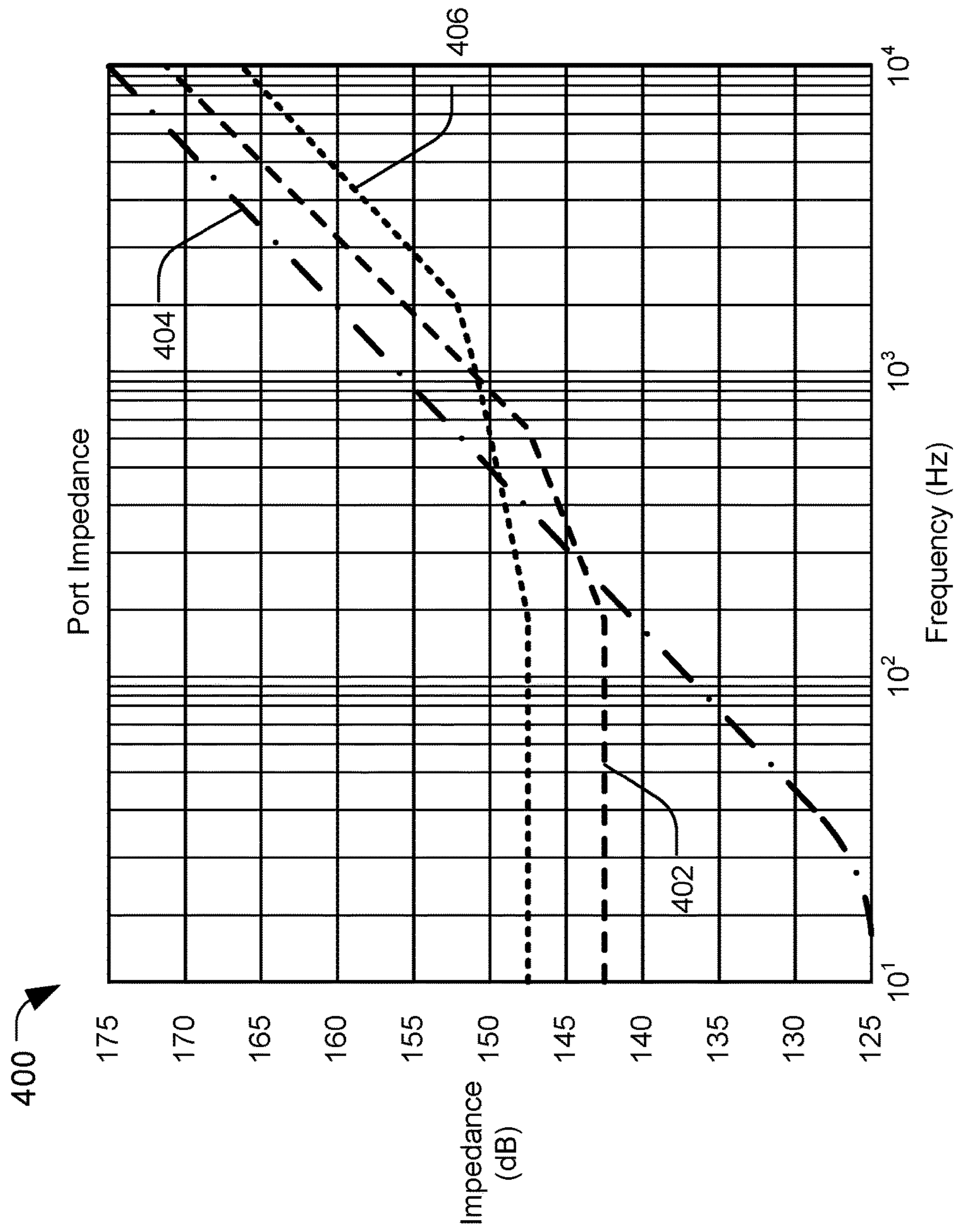
FIG. 4 shows a graph comparing the acoustic impedance of several port configurations, including a port configured according to the principles described herein.

FIG. 4 shows a graph 400 comparing the acoustic impedance of several port configurations, including a port configured according to the principles described herein. The graph plots acoustic impedance vs. frequency for three port configurations: a standard in-ear PEQ (curve 402), a standard around-ear PEQ (curve 404), and a PEQ according to the principles described herein (curve 406). As shown, the resistive PEQ in curve 406 has a higher impedance at low frequencies (where the resistive component of impedance dominates) compared to a standard in-ear or around-ear PEQ. In some examples, as in FIG. 4, the resistive PEQ has a lower impedance at high frequencies (where the reactive component of impedance dominates) compared to a standard in-ear or around-ear PEQ, though in other examples, the impedance at high frequencies may be the same as, or higher than, a standard in-ear or around-ear PEQ. The impedance at high frequencies can be tuned based on the desired application by, for example, changing the length of the port. The higher impedance at low frequencies results in a lower particle velocity and displacement through the port, and thus improves linearity of the earphone, particularly at low frequencies, while maintaining or increasing low frequency output. The PEQ port 119 facilitates avoidance of an overpressure condition when, e.g., the earphone 100 is inserted into or removed from the user's ear 10, or during use of the earphone. Pressure built up in the front acoustic chamber 114 escapes to the rear acoustic chamber 112 via the PEQ port 119, and from there to the environment via one or more back cavity ports. In one example, the back cavity includes two ports 122 and 124 (discussed in more detail below), but in other examples may include only one of these ports. Additionally, the PEQ port 119 can be used to provide a fixed amount of leakage that acts in parallel with other leakage that may be present. This leakage helps to standardize the earphone response across individuals.

The rear chamber 112 is sealed around the back side of the driver 116 by the shell 113, except that the rear chamber 112 includes one or both of a reactive element, such as a port (also referred to as a mass port) 122, and a resistive element, which may also be formed as a port 124. The reactive port 122 and the resistive port 124 acoustically couple the rear acoustic chamber 112 with an environment external to the earphone, thereby relieving the air pressure mentioned above. Although this disclosure refers to ports as reactive or resistive, in practice any port will have both reactive and resistive effects. The term used to describe a given port indicates which effect is dominant. A reactive port, like the reactive port 122, may include a tube-shaped opening in what may otherwise be a sealed acoustic chamber (e.g., the rear chamber 112). A resistive element, like the resistive port 124, may include a small opening in the wall of an acoustic chamber covered by a material providing an acoustical resistance. The material may include a wire or fabric screen that allows some air and acoustic energy to pass through the wall of the chamber, and may comprise most any porous material.

The reactive port 122 preferably has a diameter of between about 0.5 mm to about 2 mm. The reactive port 122 preferably has a length of between about 5 mm to about 25 mm. The resistive port 124 preferably has a diameter of about 1.7 mm and a length of preferably about 1 mm, and is covered with a 260 MKS Rayls resistive material (e.g., cloth or any other suitable material). These dimensions provide both the acoustic properties desired of the reactive port 122, and an escape path for the pressure built up in the front chamber 114 and transferred to the rear chamber 112 by the port 119. The total absolute value impedance from the front chamber 114 through the PEQ port 119 and out the back chamber ports 122 and 124 is preferably less than about $4\times10^{8}$ $kg/m^4\times sec$ at 10 Hz. In another example, the total absolute value impedance may be less than about $2\times10^{8}$ $kg/m^4\times sec$ at 10 Hz. The ports 122 and 124 provide porting from the rear acoustic chamber 112 to an environment external to the earphone. Furthermore, to receive a meaningful benefit in terms of passive attenuation when using a front to back PEQ port 119 in a ported system, the ratio of the impedance of the ports 122 and 124 to the impedance of the PEQ port 119 is preferably greater than 0.25 and more preferably around 1.6 at 1 kHz.

The ports 119, 122 and 124 function to increase the output of the system, which improves active noise reduction, and to provide pressure equalization. In ANR earphones, it is desirable to maximize the impedance of these ports at frequencies that can improve the total system noise reduction. It may be preferable for the impedance to be low at certain frequencies for venting pressure, while it may be preferable for the impedance to be high at other frequencies to increase low frequency output and/or to maximize passive attenuation. Ports enable such impedance tuning to occur as they can have both a resistive DC component and a reactive frequency dependent component depending upon their design, and the values of each of those components can be optimized for a desired application.

Each of the cushion 106, cavities 112 and 114, driver 116, acoustic resistance element 118, PEQ port 119, and ports 122 and 124 have acoustic properties that may affect the performance of the earphone 100. These properties may be adjusted to achieve a desired frequency response for the earphone. Additional elements, such as active or passive equalization circuitry, may also be used to adjust the frequency response. The rear chamber 112 preferably has a volume of between about 0.1 $cm^3$ to about 3.0 $cm^3$, and more preferably has a volume of about 0.5 $cm^3$ (this volume includes a volume behind a diaphragm of the driver 116 (inside the transducer), but does not include a volume occupied by metal, PCB, plastic or solder). Excluding the driver, the front chamber 114 preferably has a volume of between about 0.05 $cm^3$ to about 3 $cm^3$, and more preferably has a volume of about 0.25 $cm^3$.

In some examples, the reactive port 122 and the resistive port 124 provide acoustical reactance and acoustical resistance in parallel, meaning that they each independently couple the rear chamber 112 to free space. In contrast, reactance and resistance can be provided in series in a single pathway, for example, by placing a resistive element such as a mesh screen inside the tube of a reactive port. Parallel reactive and resistive elements, embodied as a parallel reactive port and resistive port, provides increased low frequency response compared to an embodiment using a series reactive and resistive elements. The parallel resistance does not substantially attenuate the low frequency output while the series resistance does. Using a small rear cavity with parallel ports allows the earphone to have improved low frequency output and a desired balance between low frequency and high frequency output.

Some or all of the elements described above can be used in combination to achieve a particular frequency response (non-electronically). In some examples, additional frequency response shaping may be used to further tune sound reproduction of the earphones. One way to accomplish this is with passive electrical equalization using circuitry. Such circuitry can be housed in-line with the earphones, for example, inside the electronics module 204 (FIG. 2A). If active noise reduction circuitry or wireless audio circuitry is present, such powered circuits may be used to provide active equalization.

Figure 5:
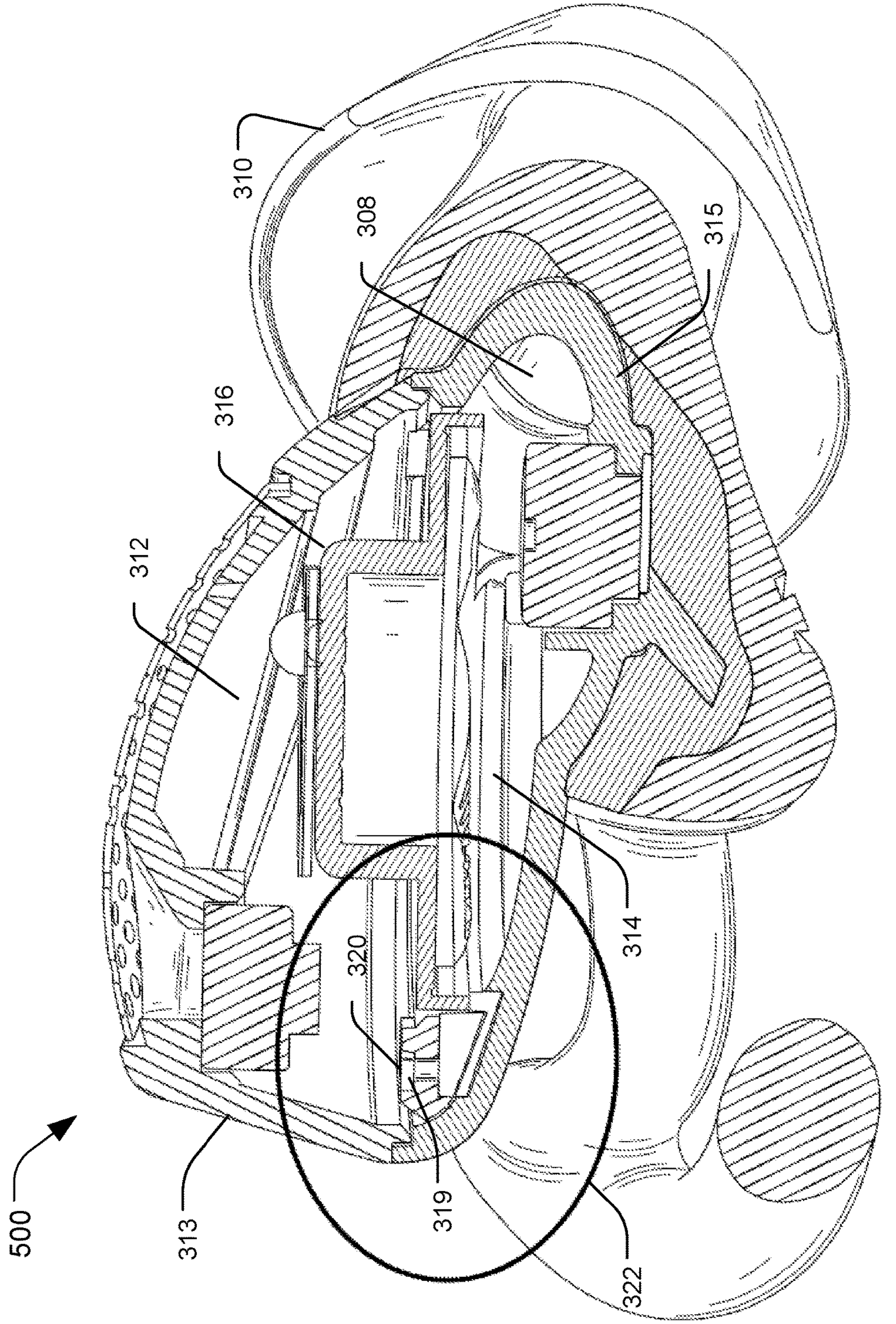
FIG. 5 is a schematic cross section of a second example of an earphone.
Figure 6:
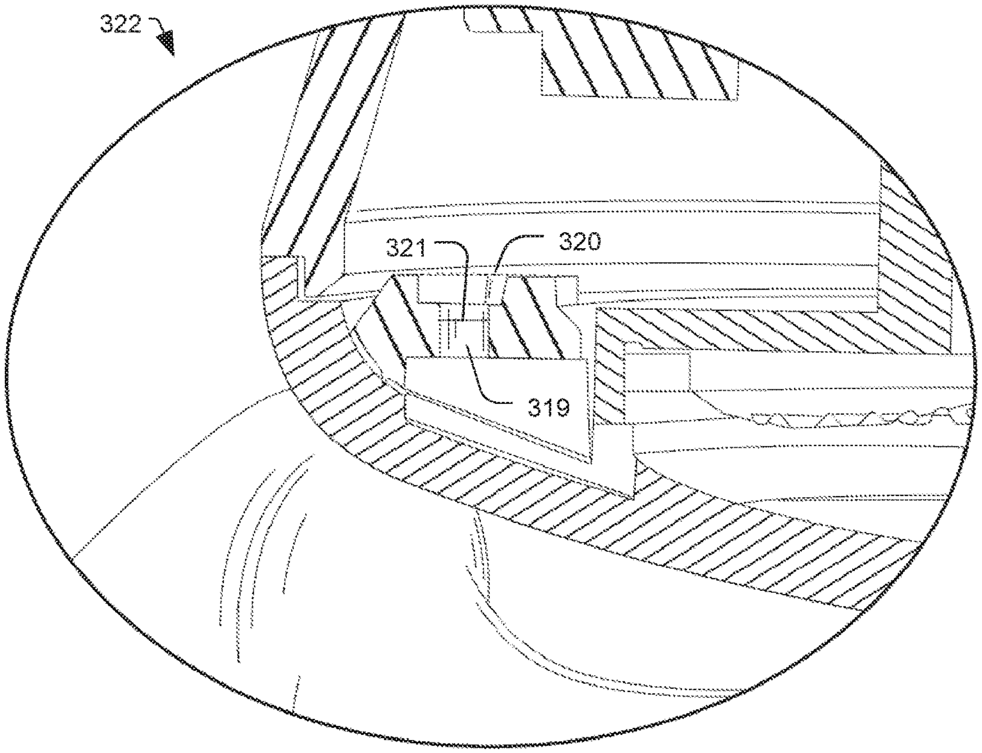
FIG. 6 is a magnified view of a portion of the earphone of FIG. 4.

In FIGS. 5 and 6, another example of an earphone 500 includes a rear acoustic chamber 312 and a front acoustic chamber 314 defined by shells 313 and 315 of the housing, respectively, on either side of a driver (i.e., acoustic transducer) 316. In some examples, a 14.8 mm diameter driver is used. Other sizes and types of acoustic transducers could be used depending, for example, on the desired frequency response of the earphone. The driver 316 separates the front and rear acoustic chambers 314 and 312. The front chamber 314 may include a nozzle 308 and an ear tip 310 that couple the front chamber 314 to the user's ear (not shown). In other examples, nozzle 308 may be omitted.

As in FIG. 3, a PEQ port 319 acoustically couples the front chamber 314 and the rear acoustic chamber 312. While the PEQ port 119 is shown as having a generally straight configuration, in other examples, it could be curved (as shown, for example, in FIG. 3). The PEQ port 319 serves to relieve air pressure that could be built up within the ear canal and front chamber 314 during over pressure events (e.g. when the earphone 300 is inserted into or onto the ear). As discussed above, that pressure is then released into the environment through one or more ports in the rear chamber 314. As in FIG. 3, resistive mesh 320 is positioned at or proximate (in another implementation, the resistive mesh 321 is inside of) the PEQ port 319. The PEQ port 319 preferably has the same area and length dimensions and acoustic impedance characteristics discussed with regard to FIG. 3. In addition, the resistive mesh 320 preferably has the same material characteristics discussed with regard to FIG. 3. While PEQ port 319 is shown in FIG. 5 as venting between the front and back cavities, in other examples the PEQ port 319 could vent from the front cavity to an environment external to the earphone.

The rear chamber 312 is sealed around the back side of the driver 316 by the shell 313, except that the rear chamber 312 includes one or both of a reactive element, such as a port (also referred to as a mass port), and a resistive element, which may also be formed as a port (not shown in this sectional view). The reactive element and the resistive element acoustically couple the rear acoustic chamber 312 with an environment external to the earphone. The reactive element and the resistive element preferably have the same dimensions and characteristics that were mentioned above with regard to FIG. 3.

Increasing the impedance of the port at low frequencies results in several important effects. For example, the port configuration improves linearity, particularly at low frequencies, and increases low frequency output for the system. In addition, the port configuration adds damping to the system at high frequencies and helps control resonance. Compared to a traditional port, the port described herein may have relatively little mass in series with the resistive component, and the mass component may be used to provide control over the shape of the higher frequency response. The characteristics of the resistive mesh and the area of the port may be adjusted to set or otherwise affect the resistance and mass of the system.

Figure 7:
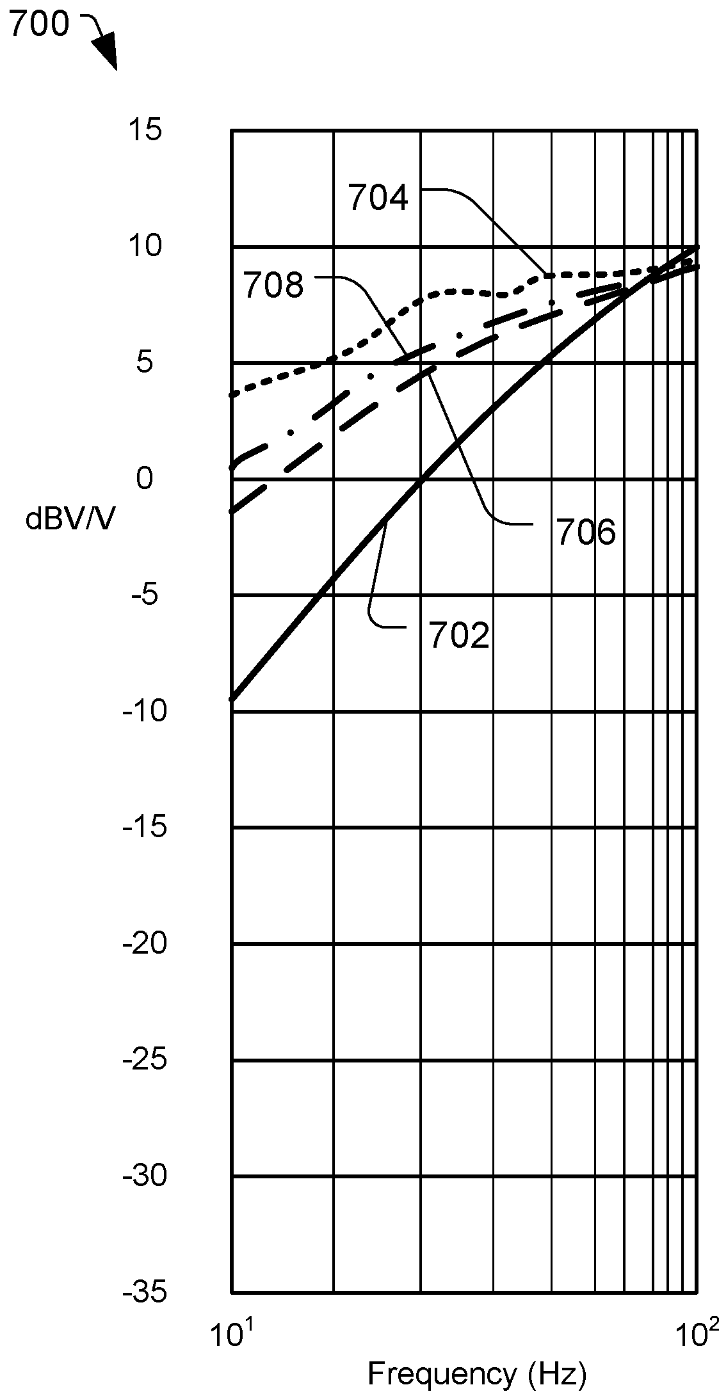
FIG. 7 shows a graph plotting acoustic output vs. frequency for low and high signal levels in an earphone incorporating a traditional port and an earphone incorporating a port according to the principles described herein.

FIG. 7 shows a graph 700 plotting acoustic output vs. frequency for low signal levels (e.g., less than 50 mV) and high signal levels (e.g., greater than 500 mV) in an earphone incorporating a traditional port and an earphone incorporated a port according to the principles described herein. The curves in FIG. 7 were generated by measuring the frequency response of the earphone at the ear canal via, e.g., a reference microphone. In an ANR system, the frequency response could also be measured using the feedback microphone, with the expectation that this measurement would yield results similar to those shown in FIG. 7 from a linearity perspective. In FIG. 7, curves 702 and 704 show the frequency response in an earphone incorporating a traditional port at low and high signal levels, respectively. As shown, at frequencies below 100 Hz, there is a difference of almost 15 dB in the response at low and high signal levels. Thus, the response for an earphone incorporating traditional port is relatively non-linear at low frequencies. Curves 706 and 708 show the frequency response in an earphone incorporating a port according to the principles described herein at low and high signal levels, respectively. As shown, there is a much smaller difference in the response at low and high signal values (i.e., the gap between the two curves has narrowed substantially). This improvement in linearity mitigates issues with audible distortion and, in ANR systems, mitigates artifacts and issues with instabilities and over-pressure of the microphone. In addition, using a port according to the principles described herein, the output at low signal values has increased by about 6 db. In an ANR system, this increased output at low signal levels results in more effective and efficient noise cancellation, increases the amount of low frequency attenuation, and improves the useful range of the earphone.

Traditionally, linearity has been improved by increasing the area and length of the PEQ, and thus reducing the resistive component while maintaining or increasing the reactive component of acoustic impedance. By contrast, in the examples described herein, the resistive component of acoustic impedance is increased. It would have been expected that increasing the resistance of the port would negatively impact buffet performance due to the associated increased resistance in the pressure venting path. However, by adjusting the area of the port and the resistance provided by the mesh material, the linearity of the port, and therefore the linearity of the earphone as measured at the ear, was improved. This improvement in linearity enabled an increased impedance at low frequencies while providing the same or improved buffet performance.

Figure 8:
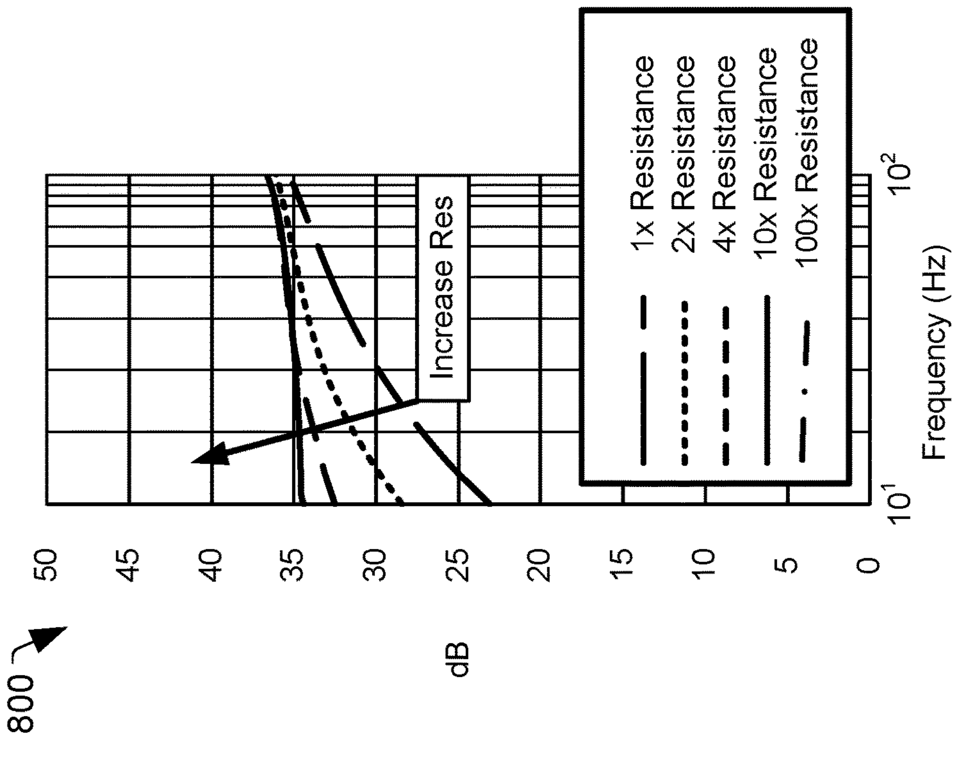
FIG. 8 shows a graph showing the effects of adjusting a resistive impedance of a port with respect to tuning a frequency response of an earphone.
Figure 9:
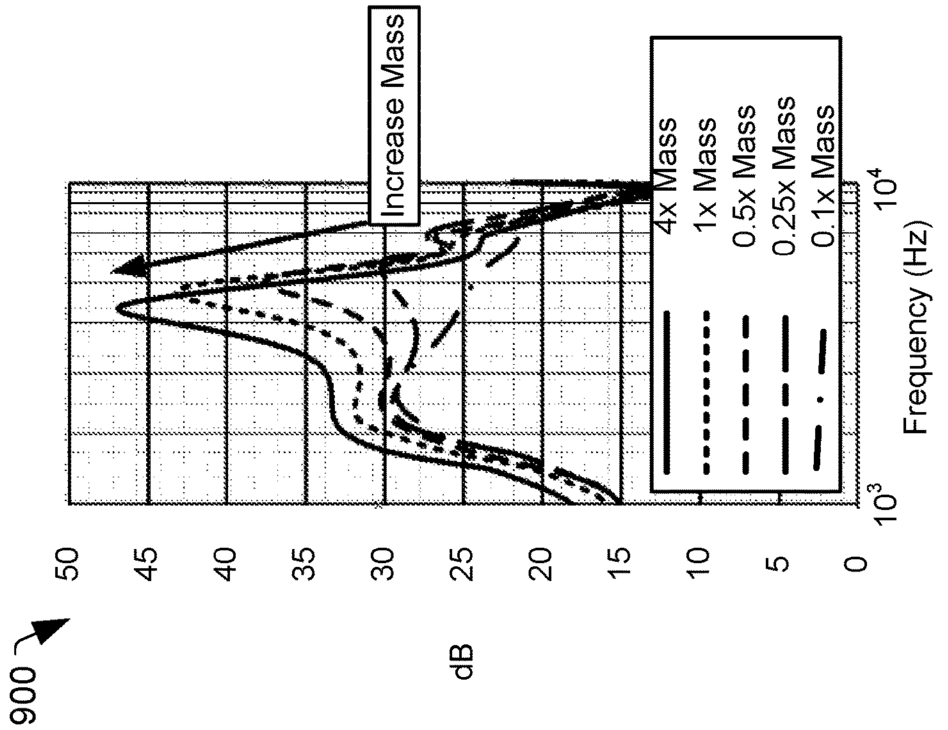
FIG. 9 shows a graph showing the effects of adjusting a mass of a port with respect to tuning a frequency response of an earphone.

FIGS. 8 and 9 show graphs 800 and 900 that illustrate the effects of varying the resistance and mass (reactance), respectively, of a port according to the principles described herein. As shown in those figures, adjusting the resistive impedance of the port (via its dimensions and the resistive material) and/or adjusting the mass of the port (via its dimensions) each enable tuning of a desired frequency response for the earphone. As shown in FIG. 8, as resistive impedance increases, the low frequency output increases, and as shown in FIG. 9, as reactive impedance decreases, damping is improved at higher frequencies.

To control variation in the front cavity at high frequencies due to ear canal effects, a mass element may be placed between the headphone front cavity and ear canal. In some examples, this mass element may take the form of a nozzle, as described in U.S. Pat. No. 7,916,888, which is incorporated by reference in its entirety. The use of a port according to the principles described herein may reduce the ear canal variation effect and allow for a similar amount of variation without the need for a mass element such as a nozzle.

A number of implementations have been described. Nevertheless, it will be understood that additional modifications may be made without departing from the scope of the inventive concepts described herein, and, accordingly, other embodiments are within the scope of the following claims.

What is claimed is:

1. An earphone comprising:

an acoustic transducer;

a housing comprising:

a first acoustic chamber acoustically coupled to a first side of the acoustic transducer;

a second acoustic chamber acoustically coupled to a second side of the acoustic transducer; and a port acoustically coupling the first acoustic chamber and the second acoustic chamber, wherein the port has a cross-sectional area that ranges from about $0.4\times10^{-6}$ m$^2$ to about $40\times10^{-6}$ m$^2$; and acoustic resistive material positioned inside of the port, wherein a combination of the position of the acoustic resistive material and the cross-sectional area of the port causes a frequency response of the earphone to be substantially linear at low frequencies.

2. The earphone of claim 1, wherein a length of the port ranges from about 0.1 millimeters to about 10 millimeters.

3. The earphone of claim 1, wherein the acoustic resistive material has an impedance that ranges from about 10 MKS Rayls to about 20,000 MKS Rayls.

4. The earphone of claim 1, wherein the acoustic resistive material comprises at least one of: a plastic, a textile, a metal, a permeable material, a woven material, a screen material, and a mesh material.

5. The earphone of claim 1, wherein active noise cancellation circuitry is coupled to the housing via a wire.

6. The earphone of claim 1, wherein the first acoustic chamber is separated from the second acoustic chamber by the acoustic transducer.

7. The earphone of claim 1, wherein a frequency response of the earphone is approximately the same at high and low signal values at frequencies below 100 Hz.

8. The earphone of claim 1, wherein a difference in a frequency response of the earphone at low signal values and a frequency response of the earphone at high signal values is less than 3 dB at frequencies between 10 and 100 Hz.

9. The earphone of claim 1, wherein the port provides damping in a frequency response of the acoustic transducer at high frequencies.

10. The earphone of claim 1, wherein the port has a resistive component of acoustic impedance of between about $2\times10^6$ acoustic ohms and about $8\times10^7$ acoustic ohms at low frequencies.

11. An apparatus comprising:

an acoustic transducer;

active noise cancellation circuitry;

a housing comprising:

a first acoustic chamber at least partially enclosing the acoustic transducer; and a port proximate the first acoustic chamber, wherein the port has acoustic resistive material positioned inside the port and has a cross-sectional area that ranges from about $0.4\times10^{-6}$ m$^2$ to about $40\times10^{-6}$ m$^2$, and wherein a combination of the position of the acoustic resistive material and the cross-sectional area of the port causes a frequency response of the earphone to be approximately the same at high and low signal values at frequencies below 100 Hz.

12. The apparatus of claim 11, wherein the port acoustically couples the first acoustic chamber to an environment external to the earphone.

13. The apparatus of claim 11, wherein the port acoustically couples the first acoustic chamber to a second acoustic chamber.

14. The apparatus of claim 11, wherein a length of the port ranges from about 0.1 millimeters to about 10 millimeters.

15. The apparatus of claim 11, wherein the acoustic resistive material has an impedance that ranges from about 10 MKS Rayls to about 20,000 MKS Rayls.

16. The apparatus of claim 11, wherein the acoustic resistive material comprises at least one of: a plastic, a textile, a metal, a permeable material, a woven material, a screen material, and a mesh material.

17. The apparatus of claim 11, wherein a frequency response of the earphone is substantially linear at low frequencies.

18. The apparatus of claim 11, wherein a difference in a frequency response of the earphone at low signal values and a frequency response of the earphone at high signal values is less than 3 dB at frequencies between 10 and 100 Hz.

19. The apparatus of claim 11, wherein the port provides damping in a frequency response of the acoustic transducer at high frequencies.

20. The apparatus of claim 11, further comprising a resistive port.

21. The apparatus of claim 11, wherein the port has a resistive component of acoustic impedance of between about $2\times10^6$ acoustic ohms and about $8\times10^7$ acoustic ohms at low frequencies.

22. The apparatus of claim 21, wherein the port has a resistive component of acoustic impedance of between about $2\times10^6$ acoustic ohms and about $8\times10^7$ acoustic ohms at low frequencies.

23. An earphone comprising:

an acoustic transducer;

a housing comprising:

a first acoustic chamber acoustically coupled to a first side of the acoustic transducer;

a second acoustic chamber acoustically coupled to a second side of the acoustic transducer; and a port acoustically coupling the first acoustic chamber and the second acoustic chamber, wherein the port has a cross-sectional area that ranges from about $0.4\times10^{-6}$ $m^2$ to about $40\times10^{-6}$ $m^2$; and acoustic resistive material positioned inside of the port, wherein a combination of the position of the acoustic resistive material and the cross-sectional area of the port causes a difference in a frequency response of the earphone at low signal values and a frequency response of the earphone at high signal values to be less than 3 dB at frequencies between 10 and 100 Hz.

* * * * *